US007759525B2

(12) United States Patent
Dubois et al.

(10) Patent No.: US 7,759,525 B2
(45) Date of Patent: Jul. 20, 2010

(54) PROCESS FOR PREPARING PARTIAL OXIDATION PRODUCTS OF LOWER ALCOHOLS BY DIRECT OXIDATION OF A LOWER ALCOHOL AND CATALYSTS FOR USE IN THAT PROCESS

(75) Inventors: Jean-Luc Dubois, Millery (FR); Markus Brandhorst, Lyons (FR); Mickaël Capron, Hasnon (FR); Christophe Dujardin, Lille (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 11/992,253

(22) PCT Filed: Sep. 20, 2005

(86) PCT No.: PCT/IB2005/053098

§ 371 (c)(1),
(2), (4) Date: Aug. 25, 2008

(87) PCT Pub. No.: WO2007/034264

PCT Pub. Date: Mar. 29, 2007

(65) Prior Publication Data

US 2009/0105507 A1    Apr. 23, 2009

(51) Int. Cl.
*C07C 41/50* (2006.01)
*C07C 43/30* (2006.01)
(52) U.S. Cl. ..................................... 568/593; 568/594
(58) Field of Classification Search .................. 502/311, 502/312; 568/490, 594
See application file for complete search history.

(56) References Cited

U.S. PATENT DOCUMENTS

| 6,054,228 | A | 4/2000 | Cisar et al. |
| 6,403,841 | B1 | 6/2002 | Iwasawa et al. |
| 6,737,545 | B1 | 5/2004 | Hibst et al. |
| 6,921,836 | B1 | 7/2005 | Hibst et al. |
| 2004/0249183 | A1 | 12/2004 | Dieterle et al. |
| 2005/0059839 | A1 | 3/2005 | Liu et al. |
| 2005/0154226 | A1 | 7/2005 | Liu et al. |

FOREIGN PATENT DOCUMENTS

DE    103 60 058    7/2004

WO    WO 99/51343    10/1999

OTHER PUBLICATIONS

Tsutsumi, Y. et al., "Direct Type Polymer Electrolyte Fuel Cells using Methoxy Fuel," Electrochemistry, vol. 70, No. 12, 2002, pp. 984-987. (Spec, p. 2).
Yuan, Y. et al., "The new catalytic property of supported rhenium oxides for selective oxidation of methanol to methylal," Chem. Commun., 2000, pp. 1421-1422. (Spec, p. 2).
Yuan, Y. et al., "Performance and Characterization of Supported Rhenium Oxide Catalysts for Selective Oxidation of Methanol to Methylal," J. Phys. Chem., 2002, vol. 106, pp. 4441-4449. (Spec, p. 2).
Yuan, Y. et al., "Selective methanol conversion to methylal on Re-Sb-O crystalline catalysts: catalytic properties and structural behavior," Topics in Catalysis, vol. 22, No. 112, Jan. 2003, pp. 9-15. (Spec, p. 3).
Yuan, Y. et al., "Selective Synthesis of Methylal from Methanol on a New Crystalline $SbRe_2O_6$ Catalyst," The Chemistry Society of Japan, 2000, pp. 674-675. (Spec, p. 3).
Yuan, Y. et al., "Performance and Characterization of a New Crystalline $SbRe_2O_6$ Catalyst for Selective Oxidation of Methanol to Methylal," Journal of Catalyst, vol. 195, 2000, pp. 51-61. (Spec, p. 3).
Liu, H. et al., "Selective One-Step Synthesis of Dimethoxymethane via Methanol or Dimethyl Ether Oxidation . . . ," J. Phys. Chem, 2003, vol. 107, pp. 10840-10847. (Spec, p. 3).
Fournier, M. et al., "Evidence of . . . ," J. Chem. Soc., Chem. Commun., 1994, pp. 307-308. (Spec, p. 3).
Tatibouët, J. M. et al., "Catalytic Oxidation of Methanol by 12-Molybdosilicic Acid Supported on Silica: Disperson Effect," J. Chem. Soc., Chem. Commun., 1988, pp. 1260-1261. (Spec, p. 4).
Liu, H. et al., "Selective Oxidation of Methanol and Ethanol on Supported Ruthenium Oxide Clusters at Low Temperatures," J. Phys. Chem., vol. 109, pp. 2155-2163. (Spec, p. 4).
Sambeth, J. et al., "Study of the Adsorption/Oxidation of Methanol over Vanadium Pentoxide," 1995, pp. 171-180. (Spec, p. 4).
International Search Report, Jun. 6, 2006.

*Primary Examiner*—Sikarl A Witherspoon
(74) *Attorney, Agent, or Firm*—Collard & Roe, P.C.

(57) ABSTRACT

The use of a complex oxide having the following composition (I). $Mo_{12}V_aX^1_bX^2_cX^3_dX^4_eO_x$ (I) wherein Mo is molybdenum; V is vanadium; O is oxygen; $X^1$ is at least one element selected from tungsten, titanium, tantalum and niobium; $X^2$ is at least one element selected from copper, antimony, tellurium and bismuth; $X^3$ is at least one element selected from alkaline earth metals; $X^4$ is at least one element selected from alkaline metals; and $0<a\leq10$; $0\leq b\leq4$; $0<c\leq5$; $0\leq d\leq2$; $0\leq e\leq2$; and x is a numerical value determined by the extents of the oxidation of the other elements, as a catalyst in the preparation of a partial oxidation product of a lower alcohol by direct oxidation of a lower alcohol in the vapor phase.

20 Claims, No Drawings

PROCESS FOR PREPARING PARTIAL OXIDATION PRODUCTS OF LOWER ALCOHOLS BY DIRECT OXIDATION OF A LOWER ALCOHOL AND CATALYSTS FOR USE IN THAT PROCESS

CROSS REFERENCE TO RELATED APPLICATIONS

Applicants claim priority under 35 U.S.C. §119 and under 35 U.S.C. §365 of PCT/IB2005/053098 filed Sep. 20, 2005. The international application under PCT article 21(2) was published in English.

The present invention relates to catalysts for a lower alcohol oxidation and to a manufacturing process for a partial oxidation product of a lower alcohol using said catalysts.

A lower alcohol in the present invention refers to alcohols having 1 to 4 carbon atoms, that is, methanol, ethanol, propanol and butanol. Specific examples of a partial oxidation product of a lower alcohol of the present invention include dialkoxymethane such as dimethoxymethane (also called methylal or formaldehyde dimethyl acetal).

In the method for manufacturing a partial oxidation product of a lower alcohol, the lower alcohol is subjected to vapor phase contact oxidation with a molecular oxygen containing gas in the presence of the lower alcohol oxidation catalyst.

Particularly, the present invention relates to the one-stage preparation by direct oxidation of dimethoxymethane from methanol:

$$3CH_3OH + \tfrac{1}{2}O_2 \rightarrow CH_3OCH_2OCH_3 + 2H_2O$$

Methylal can find many applications in various areas, due to its exceptional properties: an exceptional solvent power; its amphiphilic character: methylal is both hydrophilic and lipophilic; a low viscosity; a low surface tension; a particularly high evaporation rate.

Methylal finds applications in the following fields: aerosols for cosmetic and technical applications; paints and varnishes (as a solvent); paint strippers; cleaning and degreasing solvents; pharmaceuticals (as a carrier, or as a reagent); in the synthesis of resins; adhesives (quick drying); extraction (flavorings, fragrances and aromas); diesel fuel additives; insecticides; fuel cells. Y. Tsutsumi et al. Electrochemistry, 70(12) (2002) 984 and U.S. Pat. No. 6,054,228 B1 describe applications of methylal in fuel cells. In particular, the methylal is a reagent in the production of polyoxymethylenedimethylethers used as a fuel in fuel cells.

For the direct oxidation of methanol to methylal several solutions have been described in the past.

U.S. Pat. No. 6,403,841 B1 discloses a method for manufacturing methylal by partial oxidation of methanol on a catalyst made of a rhenium-antimony compound. The preferred compound is a mixed oxide $SbRe_2O_6$. Conversion of 12.3% with methylal selectivities of 89% are disclosed. The reaction of the example is carried out in a 5 vol % methanol, 10 vol % oxygen and 85 vol % helium gas stream, at a 10 000 $h^{-1}$ space velocity. Rhenium is an expensive material, and rhenium oxide is known to be a volatile compound, making hardly feasible a commercial process based on this technology.

Y. Yuan, T. Shido and Y. Iwasawa, Chem. Comm., 2000, 1421-1422, disclose catalysts based on supported rhenium, or bulk rhenium oxides. With $Re/TiO_2$ rutile, 53.7% conversion and 83.1% selectivity are achieved at 240° C. As mentioned above, rhenium is not common in catalysts because it is rather expensive and because rhenium oxides tend to sublime under reaction conditions.

Y. Yuan and Y. Iwasawa, *J. Phys. Chem. B*, 2002, 106, 4441 describe the performances of supported rhenium oxide catalysts for the selective oxidation of methanol to methylal.

Y. Yuan, K. Tsai, H. Liu, Y. Iwasawa, *Topics in Catalysis*, Vol 22, No 1/2, Jan. 2003 describe tests conducted with mixed Re—Sb oxides as catalysts for methanol oxidation to methylal. Selectivities of 92.5% at 6.5% conversion have been obtained. These results are partly disclosed in the above mentioned U.S. Pat. No. 6,403,841 B1.

Y. Yuan, H. Liu, H. Imoto, T. Shido, Y. Iwasawa, *Chemistry Letters* 2000, 674 and *J. Catal.* 195 (2000) 51-61 describe tests conducted with rhenium and mixed oxides Re—Sb—O as catalysts in the same reaction. The results are the same as in the previous paper.

US Patent Application 2005/0154226 A1 discloses a process for the production of methylal by oxidation of methanol and/or dimethylether. The feed containing also oxygen reacts on a catalyst made of a Keggin type heteropolyacid $H_{3+n}X\text{-}V_nMO_{12-n}O_{40}$, where X represents phosphorus or silicon, and n is a value from 0 to 4. The best results seem to be obtained on the $SiO_2$-supported catalyst $H_5PV_2Mo_{10}O_{40}/SiO_2$. Selectivities as high as 61.8% to methylal are achieved at about 40% conversion. This work has also been published in *J. Phys. Chem. B* 2003, 107, 10840-10847.

M. Fournier, A. Aouissi and C. Rocchicciolo-Deltcheff, *J. Chem. Soc., Chem. Commun.* 1994, 307-308 describe the evaluation of supported phosphomolybdic acid $H_3PMo_{12}O_{40}$/silica, after heat treatment, as catalysts in methanol oxidation. A high selectivity to methylal was observed after a heat treatment at 320° C. The authors linked this high selectivity to the presence of a βMoO3 phase.

J M. Tatibouët, M. Che, M. Amirouche, M. Fournier, C. Rocchiccioli-Deltcheff, *J. Chem. Soc., Chem. Commun.* 1998, 1260-1261 describe that supported silicomolybdic acid $H_4SiMO_{12}O_{40}$/silica at low surface coverage, can lead to methylal at about 30% selectivity.

US Patent Application 2005/0059839 A1 discloses catalysts for the oxidation of methanol to methylal but the selectivities are rather low in most examples. The catalysts are supported platinum group metals. Similar work is published in *J. Phys. Chem. B* 2005, 109, 2155-2163. This paper concerns supported Ruthenium Oxides. This kind of catalyst are also rather expensive as it requires expensive raw materials.

J. Sambeth, L. Gambaro and H. Thomas, *Adsorption Science Technology* (1995) page 171, have used vanadium pentoxide was used for the oxidation of methanol, methylal being among the products.

None of these known catalysts for the preparation of a partial oxidation product of a lower alcohol (such as methylal) by a direct oxidation of a lower alcohol (methanol) gives a complete satisfaction.

An object of the present invention is to provide an alternative to these known catalysts, notably for making feasible a commercial process.

Another object of the present invention is to provide a catalyst that is highly active and has a high selectivity for the direct oxidation of methanol to methylal.

Still another object of the invention is to provide a process for the selective oxidation of methanol to methylal.

To that end, the present invention relates to the use of a complex oxide having the following composition (I):

$$Mo_{12}V_aX^1_bX^2_cX^3_dX^4_eO_x \qquad (I)$$

wherein:

Mo is molybdenum;
V is vanadium;

O is oxygen;

X$^1$ is at least one element selected from tungsten, titanium, tantalum and niobium;

X$^2$ is at least one element selected from copper, antimony, tellurium and bismuth;

X$^3$ is at least one element selected from alkaline earth metals;

X$^4$ is at least one element selected from alkaline metals; and $0 < a \leq 10$, preferably $3 \leq a \leq 4$;

$0 \leq b \leq 4$, preferably $0.5 \leq b \leq 2$;

$0 < c \leq 5$, preferably $0 < c \leq 4$;

$0 \leq d \leq 2$;

$0 \leq e \leq 2$; and x is a numerical value determined by the extents of the oxidation of the other elements, as a catalyst in the preparation of a partial oxidation product of a lower alcohol by direct oxidation of a lower alcohol in the vapor phase.

Copper and/or antimony are preferred as X$^2$.

The alkaline earth metal X$^3$ is preferably selected among magnesium, calcium, strontium and barium.

The alkaline metal X$^3$ is preferred selected among potassium, rubidium and cesium.

The catalyst according to the present invention can have a monocomponent structure. However, it can also have a multicomponent structure, in particular a bicomponent or tricomponent structure. Such structures are described for example in U.S. Pat. No. 6,737,545, US 2004/0249183, DE 10360058 and U.S. Pat. No. 6,921,836.

The catalyst according to the present invention can be shaped as a bulk catalyst or it can be a supported catalyst.

According to a preferred embodiment of the present invention, the catalyst has the following composition:

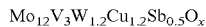

$\text{Mo}_{12}\text{V}_3\text{W}_{1.2}\text{Cu}_{1.2}\text{Sb}_{0.5}\text{O}_x$ x being a numerical value determined by the extents of the oxidation of other elements.

Different metal oxides entering in the composition of the mixed oxide of formula (I) can be used as raw materials in the preparation of this composition, but the raw materials are not limited to the oxides; other raw material can be cited, in particular:

in the case of molybdenum, ammonium molydate and mobdylic acid and in the case of tungsten, ammonium tungstate and tungstic acid;

in the case of vanadium, ammonium metavanadate;

in the case of bismuth, nitrates, carbonates and hydroxides, such as bismuth nitrate;

in the case of antimony, antimony acetate;

in the case of titanium, titane chloride; and in the case of copper, copper sulfate;

and, generally, any compound capable of forming an oxide by calcination, i.e. organic acid salts, mineral acid salts, complex metallic compounds, organic metallic compounds, etc.

The preparation of the catalysts of the present invention can be done by any process well-known by the man skilled in the art for the preparation of catalyst in general, using well-known steps: preparing a slurry of oxides or of compounds capable of forming oxides, drying, calcination, powdering, crushing, shaping (preparing grains of catalytically active material coated on supports such as balls, preparing extruded grains, . . . ). Steps can be repeated: precalcination, calcination, etc.

In particular, a composition of mixed oxides of Formula (I) can be used, which has been obtained by the process including the following steps:

preparing a slurry of oxides or of compounds capable of forming oxides of Formula (I) by calcination;

drying of said slurry possibly followed by a precalcination of the dried product for obtaining the solid of Formula (I);

crushing of this solid; and calcination.

Usually the catalyst is activated in the reactor before starting the reaction.

The present invention also relates to a process for manufacturing a partial oxidation product of a lower alcohol wherein a lower alcohol is subjected to vapor phase contact oxidation with a molecular oxygen containing gas in the presence of a catalyst, characterized by the fact that a catalyst of composition (I) as described above is used.

The vapor phase contact oxidation can be conducted at a temperature of 100-400° C., preferably of 200-300° C., at a pressure of 50-1000 kPa, preferably of 100-500 kPa.

The space velocity can be of 2000-100000 hr$^{-1}$, preferably of 11000-44000 hr$^{-1}$, on the basis of the active material only.

The lower alcohol concentration in the flow can be from 1 to 60%, preferably from 3 to 50%.

The molar ratio of oxygen (calculated as $O_2$) to lower alcohol can be of 0.5:6 to 3:1, preferably of 0.5:3 to 2:1.

The molecular oxygen containing gas can be pure oxygen gas or air.

A diluent gas can be added to the reactants, said diluent gas constituting particularly 40 to 90 vol % of the gaseous stream.

The diluent can be selected among nitrogen, carbon dioxide, a rare gas such as helium and argon, and inert gas such as water vapor, and mixtures of these gas.

According to a particular embodiment of the process of the invention, a raw material gas composed of a mixed gas in which the molecular oxygen containing gas and possibly the diluent gas have been added to a lower alcohol, is introduced into a fixed bed reactor containing the catalyst.

As mentioned above, the lower alcohol is preferably methanol, the partial oxidation product of the lower alcohol being methylal.

The present invention will now be described in more specific terms through examples, but the scope of the present invention is not restricted to these examples.

DMM is the abbreviation for dimethoxymethane (methylal).

The conversion, selectivity and yield referred to in the examples are expressed by the following equations:

Methanol conversion was calculated as (moles of reacted methanol)/(moles of supplied methanol)×100.

DMM selectivity was calculated as (moles of produced DMM)×3/(moles of reacted methanol)×100.

DMM yield was calculated as the number of moles of product×number of carbon atoms in the product/(moles of supplied methanol)×100.

EXAMPLE 1

Preparation of Catalyst

The catalyst

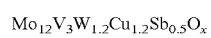

$\text{Mo}_{12}\text{V}_3\text{W}_{1.2}\text{Cu}_{1.2}\text{Sb}_{0.5}\text{O}_x$ x being the amount of oxygen bound to other elements, is prepared as follows:

In a flask, equipped with a stirring motor, a first solution (solution A) is prepared with 60.0 g of deionized water at 95° C. and 1.63 g of ammonium paratungstate. Once dissolved, 1.82 g of ammonium metavanadate and 11.0 g of ammonium heptamolybdate were then added and dissolved.

0.78 g of antimony acetate (purity 99.6%) was added further.

For solution B, 1.56 g of copper sulfate was dissolved in of 9.6 g of deionized water, and the resultant solution was added into solution A to get a slurry.

The slurry was dried at about 100° C. The powder thus obtained was calcined (preliminary calcination) at 390° C. for about 5 hrs in a rotary kiln furnace, after an increase of the temperature at a rate of about 60° C. per hour from room temperature.

The shaped powder thus obtained was then crushed and once again calcined at 390° C. for 5 hrs in a rotary kiln furnace, after an increase of the temperature at a rate of about 70° C. per hour from the room temperature, to get a catalyst of the present invention.

The atomic ratio of the catalytically active component is as mentioned above.

EXAMPLE 2

Evaluation of the Catalyst

The catalyst evaluation is performed in a fixed bed flow reactor. The gas flow of Helium and Oxygen is adjusted using mass flow controllers. The gas flow passes through an evaporator/saturator filled with methanol. The evaporator is at room temperature, and the condenser is adjusted and can be lowered at −14° C. (in most experiments the temperature is adjusted to 11° C.), to control the methanol vapour pressure. The temperature of the gas is measured with a thermocouple at the top of the saturator.

The gas is fed to the reactor which is located in a furnace. The reaction temperature is measured by a thermocouple located in the catalyst bed. The effluent is sent to a condenser, to trap heavy products.

The effluent gases are analysed by an on-line microGC equipped with 2 columns (Molecular Sieve and Plot Q).

A flow of 45.7 ml/min Helium, 4.6 ml/min $O_2$ passes through the evaporator/saturator adjusted at a given temperature to lead to a gas composition of methanol/oxygen/helium 7.5/9.5/83.

75 to 300 mg of catalysts were mixed with the same amount of silicon carbide and filled in the glass reactor. The space velocity was between 11000 and 44000 $hr^{-1}$.

MicroGC calibration was carried out with reference gas mixtures. Calibration for condensable products (dimethoxymethane, methanol, methylformate) was done using the evaporator/saturator.

EXAMPLE 3

Methanol Oxidation Reaction 303 mg of the catalyst as prepared in Example 1, were loaded in the reactor.

The catalyst was first activated in Helium/oxygen (45.7 ml/min: 4.6 ml/min) mixture at 350° C., for 2 hrs. Then the temperature was decreased to 200° C., and data acquisition stated.

The oxygen and Helium flow rate were respectively 4.6 and 45.7 ml/min and the methanol concentration was adjusted to 3.9%.

The results are given in Table 1:

TABLE 1

| Temperature | $CH_3OH$ Conversion (%) | DMM Selectivity (%) | DMM Yield (%) |
|---|---|---|---|
| 200° C. | 20 | 40 | 8 |
| 250° C. | 60 | 70 | 48 |

EXAMPLE 4

Methanol Oxidation Reaction

The catalyst requires an activation in-situ to reach higher yields.

155 mg of catalyst as prepared in Example 1, were loaded in the reactor.

The catalyst was first activated in Helium/oxygen (45.7 ml/min: 4.6 ml/min) mixture at 350° C. Then the temperature was decreased to 200° C., and data acquisition stated. After 30 to 60 minutes stabilisation, the catalyst efficiency was recorded. Data are listed in the following table. After data acquisition, the catalyst temperature was increased to the next level of temperature, 250° C., 300° C. and 350° C. where data were taken.

Then the temperature was decreased to 250° C. once again, as the best selectivity had been observed at this temperature. After 60 minutes data acquisition, the temperature was once again increased to 350° C., where previous results were confirmed, and finally the temperature was decreased to 250° C., where data were taken over a 400 minutes period.

In these tests, the oxygen and Helium flow rates were respectively 4.6 and 45.7 ml/min, and the methanol concentration in the reaction feed was adjusted to 7%.

The results are given in Table 2:

TABLE 2

| Temperature | $CH_3OH$ Conversion (%) | DMM Selectivity (%) | DMM Yield (%) |
|---|---|---|---|
| 200° C. | 20 | 40 | 8 |
| 250° C. | 70 | 65 | 46 |
| 300° C. | 85 | 12 | 10 |
| 350° C. | 80 | 2 | 1.6 |
| 250° C. | 80 | 65 | 52 |
| 350° C. | 80 | 2 | 1.6 |
| 250° C. | 80 | 65 | 52 |
| 250° C. after 400 minutes | 78 | 68 | 53 |

We noticed an increase of activity after the temperature increase from 250 to 300° C. during the initial cycle.

EXAMPLE 5

Methanol Oxidation Reaction

The influence of gas hourly space velocity (GHSV) on the catalyst efficiency was studied by adjusting the weight of catalyst.

The catalyst was first activated in helium/oxygen (45.7 ml/min: 4.6 ml/min) mixture at 350° C., for 2 hrs. In these tests, the Oxygen and Helium flow rates were respectively 4.6 and 45.7 ml/min, and the methanol concentration in the reaction feed was adjusted to 6.9%.

The results are given in Table 3:

TABLE 3

| Temperature | CH₃OH Conversion (%) | DMM Selectivity (%) | DMM Yield (%) |
|---|---|---|---|
| 75 mg of catalyst | | GHSV = 44000 hr⁻¹ | |
| 250° C. | 10 | 45 | 4.5 |
| 300° C. | 38 | 30 | 11 |
| 150 mg of catalyst | | GHSV = 22000 hr⁻¹ | |
| 200° C. | 7 | 60 | 4.2 |
| 250° C. | 22 | 45 | 9.9 |
| 300° C. | 66 | 17 | 11 |
| 300 mg of catalyst | | GHSV = 11000 hr⁻¹ | |
| 200° C. | 13 | 45 | 5.9 |
| 250° C. | 42 | 50 | 21 |
| 300° C. | 85 | 18 | 15.3 |

EXAMPLE 6

Reference Example

A conventional iron molybdate catalyst, as used in the classical formaldehyde process, was used for this test.

152 mg of catalyst were loaded in the reactor. As expected for this kind of catalyst, high selectivities to DMM can be achieved at low conversion/temperature, however at 250° C. formaldehyde is the main product.

In these tests, the oxygen and Helium flow rates were respectively 4.6 and 45.6 ml/min, and the methanol concentration in the reaction feed was adjusted to 6.9%.

The results are given in Table 4.

TABLE 4

| Temperature | CH₃OH Conversion (%) | DMM Selectivity (%) | DMM Yield (%) |
|---|---|---|---|
| 150° C. | <5 | — | |
| 200° C. | 10 | 58 | 5.8 |
| 250° C. | 70 | 2 | 1.4 |

The invention claimed is:

1. A process for manufacturing a partial oxidation product of a lower alcohol wherein a lower alcohol is subjected to vapor phase contact oxidation with a molecular oxygen containing gas in the presence of a catalyst,
wherein the lower alcohol is an alkanol, and the partial oxidation product of the lower alcohol is a dialcoxyalkane,
wherein a catalyst having the following composition (I):

$$Mo_{12}V_aX^1{}_b,X^2{}_cX^3{}_dX^4{}_eO_x \qquad (I)$$

wherein:
Mo is molybdenum;
V is vanadium;
O is oxygen;
X¹ is at least one element selected from tungsten, titanium, tantalum and niobium;

X² is at least one element selected from copper, antimony, tellurium and bismuth;
X³ is at least one element selected from alkaline earth metals;
X⁴ is at least one element selected from alkaline metals; and
0<a≦10;
0≦b≦4;
0<c≦5;
0≦d≦2;
0≦e≦2; and
x is a numerical value determined by the extents of the oxidation of the other elements, is used.

2. The process according to claim 1, wherein 3≦a≦4.
3. The process according to claim 1, wherein 0.5≦b≦2.
4. The process according to claim 1, wherein 0<c≦4.
5. The process according to claim 1, wherein an alkaline earth metal X³ is selected among Magnesium, Calcium, Strontium and Barium.
6. The process according to claim 1, wherein an alkaline metal x⁴ is selected among potassium, rubidium and cesium.
7. The process according to claim 1, wherein the catalyst has a multicomponent structure, in particular a bicomponent or tricomponent structure.
8. The process according to claim 1, wherein the catalyst is shaped as a bulk catalyst.
9. The process according to claim 1, wherein the catalyst is a supported catalyst.
10. The process according to claim 1, wherein the catalyst has the following composition:

$$Mo_{12}V_3W_{1.2}Cu_{1.2}Sb_{0.5}O_x$$

x being a numerical value determined by the extents of the oxidation of other elements.

11. The process according to claim 1, wherein vapor phase contact oxidation is conducted at a temperature of 100-400° C., preferably of 200-300° C.
12. The process according to claim 1, wherein vapor phase contact oxidation is conducted at a pressure of 50-1000 kPa, preferably of 100-500 kPa.
13. The process according to claim 1, wherein the space velocity is of 2000-100000 hr⁻¹, preferably of 11000-44000 hr⁻¹, on the basis of the active material only.
14. The process according to claim 1, wherein the lower alcohol concentration in the flow is from 1 to 60%, preferably from 3 to 50%.
15. The process according to claim 1, wherein the molar ratio of oxygen (calculated as O₂) to lower alcohol is 0.5:6 to 3:1, preferably 0.5:3 to 2:1.
16. The process according to claim 1, wherein the molecular oxygen containing gas is pure oxygen gas or air.
17. The process according tof claim 1, wherein a diluent gas is added to the reactants, said diluent gas constituting particularly 40 to 90 vol % of the gaseous stream.
18. The process according to claim 17, wherein the diluent is selected among nitrogen, carbon dioxide, a rare gas such as helium and argon, and inert gas such as water vapor, and mixtures of these gas.
19. The process according to claim 1, wherein a raw material gas composed of a mixed gas in which the molecular oxygen containing gas and possibly the diluent gas have been added to a lower alcohol, is introduced into a fixed bed reactor containing the catalyst.
20. The process according to claim 1, wherein the lower alcohol is methanol and the partial oxidation product of the lower alcohol is methylal.

* * * * *